(12) United States Patent
Webber et al.

(10) Patent No.: US 9,505,707 B2
(45) Date of Patent: Nov. 29, 2016

(54) COMPOSITION AND METHOD FOR REDUCING HYDRATE AGGLOMERATION

(75) Inventors: Peter A. Webber, Sugar Land, TX (US); Peter G. Conrad, Sugar Land, TX (US); Austen K. Flatt, Sugar Land, TX (US)

(73) Assignee: NALCO Company, Naperville, IL (US)

( * ) Notice: Subject to any disclaimer, the term of this patent is extended or adjusted under 35 U.S.C. 154(b) by 922 days.

(21) Appl. No.: 13/326,910

(22) Filed: Dec. 15, 2011

(65) Prior Publication Data

US 2012/0161070 A1 Jun. 28, 2012

Related U.S. Application Data

(60) Provisional application No. 61/426,029, filed on Dec. 22, 2010.

(51) Int. Cl.
C07C 229/26 (2006.01)
C07C 237/10 (2006.01)
C07C 237/06 (2006.01)
C10L 3/10 (2006.01)
C10L 10/18 (2006.01)

(52) U.S. Cl.
CPC ............. *C07C 237/06* (2013.01); *C10L 3/107* (2013.01); *C10L 10/18* (2013.01); *C10L 2200/029* (2013.01); *C10L 2200/0259* (2013.01); *C10L 2230/14* (2013.01)

(58) Field of Classification Search
CPC ...... C09K 2208/22; C09K 8/52; C09K 8/54; C07C 229/26; C07C 211/62; C07C 211/63; C10L 10/18; C10L 3/107; C10L 2200/029; C10L 2200/0259; C10L 2230/14
USPC ......... 516/113; 564/197, 193, 291; 507/240, 507/90, 241, 244; 166/304
See application file for complete search history.

(56) References Cited

U.S. PATENT DOCUMENTS

| | | | |
|---|---|---|---|
| 2,168,253 A * | 8/1939 | Balle ................... | D06M 13/342 252/8.63 |
| 2,295,655 A * | 9/1942 | Hentrich .............. | C07C 237/00 510/131 |
| 2,317,999 A * | 5/1943 | Leuchs ................ | 564/164 |
| 2,888,383 A * | 5/1959 | Byrne ................ | 424/54 |
| 3,277,118 A * | 10/1966 | Schmid ................ | A61K 8/416 424/52 |
| 3,317,556 A | 5/1967 | Rose et al. | |
| 3,894,962 A | 7/1975 | Allain | |
| 4,022,606 A * | 5/1977 | Conrad et al. ........ | 504/159 |
| 4,652,623 A | 3/1987 | Chen et al. | |
| 4,980,378 A | 12/1990 | Wong et al. | |
| 6,702,946 B1 | 3/2004 | Huang et al. | |
| 7,311,144 B2 | 12/2007 | Conrad | |
| 7,408,004 B2 | 8/2008 | Struck et al. | |
| 7,550,339 B2 | 6/2009 | Forbes | |
| 7,989,403 B2 * | 8/2011 | Acosta ................ | C02F 1/68 106/14.16 |
| 8,288,323 B2 * | 10/2012 | Acosta ................ | C07D 241/04 166/305.1 |
| 8,394,872 B2 * | 3/2013 | Faust, Jr. ............. | C08F 220/34 523/175 |
| 8,618,025 B2 * | 12/2013 | Webber .............. | C09K 8/52 166/304 |
| 8,921,478 B2 * | 12/2014 | Conrad ................ | C08F 220/56 210/698 |
| 9,410,073 B2 * | 8/2016 | Webber .............. | C09K 8/52 |
| 2006/0094913 A1 | 5/2006 | Spratt | |
| 2010/0087339 A1 * | 4/2010 | Acosta ................ | 507/90 |
| 2010/0099807 A1 * | 4/2010 | Carlise et al. ........ | 524/377 |
| 2010/0099814 A1 * | 4/2010 | Conrad et al. ........ | 524/555 |
| 2010/0219379 A1 * | 9/2010 | Acosta et al. ........ | 252/392 |
| 2010/0222239 A1 | 9/2010 | Acosta et al. | |
| 2011/0009556 A1 * | 1/2011 | Faust et al. .......... | 524/555 |
| 2012/0149609 A1 * | 6/2012 | Tekavec et al. ...... | 507/261 |
| 2012/0157351 A1 * | 6/2012 | Webber ................ | 507/90 |
| 2012/0161070 A1 | 6/2012 | Webber et al. | |

(Continued)

FOREIGN PATENT DOCUMENTS

GB 962242 7/1964
JP 51035433 A * 3/1976

(Continued)

OTHER PUBLICATIONS

Machine Translation of Publ. No. JP 08-113703 (A), published May 1996, European patent Office, obtained online @ http://worldwide.espacenet.com/?locale=EN_ep (Dowloaded May 12, 2015) pp. 1-18.*

(Continued)

*Primary Examiner* — Daniel S Metzmaier
(74) *Attorney, Agent, or Firm* — Eric D. Babych; Brinks Gilson & Lione

(57) ABSTRACT

Disclosed and claimed is a composition and method of inhibiting the formation of hydrate agglomerates in a fluid comprising water, gas, and optionally liquid hydrocarbon. The composition comprises the following formula and the method comprises adding to the fluid an effective anti-agglomerant amount of any of the following formula and optionally salts thereof.

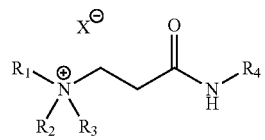

$R_1$, $R_2$, and $R_3$ are each independently $C_nH_{2n+1}$ or benzyl. $R_4$ is $C_4$-$C_{20}$ alkyl or alkenyl. n is an integer from 0 to 10. $X^-$ is a counterion.

13 Claims, No Drawings

(56) References Cited

U.S. PATENT DOCUMENTS

| | | | |
|---|---|---|---|
| 2014/0091262 A1* | 4/2014 | Webber et al. | 252/391 |
| 2014/0094393 A1* | 4/2014 | Webber | 507/90 |
| 2014/0106991 A1* | 4/2014 | Acosta et al. | 507/90 |
| 2015/0148266 A1* | 5/2015 | Webber | C09K 8/52 507/90 |
| 2016/0122619 A1* | 5/2016 | Lucente-Schultz | C09K 8/52 507/90 |
| 2016/0186039 A1* | 6/2016 | Owsik | C09K 8/52 507/90 |

FOREIGN PATENT DOCUMENTS

| | | |
|---|---|---|
| JP | 08113703 A * | 5/1996 |
| WO | 0240433 | 5/2002 |
| WO | 2004032824 | 4/2004 |
| WO | 2004041884 | 5/2004 |
| WO | WO 2005/042675 A2 | 5/2005 |
| WO | 2006051265 | 5/2006 |
| WO | 2008089262 | 7/2008 |

OTHER PUBLICATIONS

Sharma et al, "Green and mild protocol for hetero-Michael addition of sulfur and nitrogen nucleophiles in ionic liquid", Journal of Molecular Catalysis, A: Chemical, 277, pp. 215-220, (Aug. 2007).

V. Fedi et al, Insertion of an Aspartic Acid Moiety into Cyclic Pseudopeptides: Synthesis and Biological Characterization of Potent Antagonists for the Human Tachykinin NK-2 Receptor, Journal of Medicinal Chemistry, vol. 47, pp. 6935-6947, (Dec. 2004).

Billmeyer, F., Textbook of Polymer Science, John Wiley & Sons, Inc., 3rd edition, p. 5, 1984.

Nakane, Masami, et al., "7-Oxabicyvlo[2.2.1]heptyl Carboxylic Acids as Thromboxane $A_2$ Antagonists: Aza ω -Chain Analogues", *American Chemical Society*, 33:2465-2476 (1990).

Buchhammer, H.-M. et al.; "Nanoparticles based on polyelectrolyte complexes: effect of structure and net charge on the sorption capability for solved organic molecules"; Colloid Polym Sci 278: (2000); pp. 841-847.

* cited by examiner

COMPOSITION AND METHOD FOR REDUCING HYDRATE AGGLOMERATION

CROSS REFERENCE TO RELATED APPLICATION

This application claims the benefit of U.S. provisional patent application No. 61/426,029, "Composition and Method for Reducing Hydrate Agglomeration," filed on Dec. 22, 2010, which is incorporated herein in its entirety by reference.

TECHNICAL FIELD OF THE INVENTION

This invention relates generally to reducing or inhibiting the formation and growth of hydrate particles in fluids containing hydrocarbon gas and water. More specifically, the invention relates to reducing or inhibiting such formation in the production and transport of natural gas, petroleum gas, or other gases. The invention has particular relevance to treating such systems with beta-amino amide surfactants as anti-agglomerants to reduce or inhibit the formation of gas hydrates.

BACKGROUND OF THE INVENTION

Since Hammerschmidt discovered in 1934 that gas hydrates would block gas pipelines, research for the prevention of hydrate formation and agglomeration has become an important matter. Gas hydrates can be easily formed during the transportation of oil and gas in pipelines when the appropriate conditions are present. Water content, low temperatures, and elevated pressure are required for the formation of gas hydrates. The formation of gas hydrates often result on lost oil production, pipeline damage, and safety hazards to field workers. Modern oil and gas technologies commonly operate under severe conditions during the course of oil recovery and production; for instance, high pumping speed, high pressure in the pipelines, extended length of pipelines, and low temperature of the oil and gas flowing through the pipelines. These conditions are particularly favorable for the formation of gas hydrates, which can be particularly hazardous for oil productions offshore or for locations with cold climates.

Gas hydrates are ice-like solids that are formed from small nonpolar molecules and water at lower temperatures and at increased pressures. Under these conditions, the water molecules can form cage-like structures around these small nonpolar molecules (typically dissolved gases such as carbon dioxide, hydrogen sulfide, methane, ethane, propane, butane and iso-butane), creating a type of host-guest interaction also known as a clathrate or clathrate hydrate. The specific architecture of this cage structure can be one of several types (called type 1, type 2, type H), depending on the identity of the guest molecules. However, once formed, these crystalline cage structures tend to settle out from the solution and accumulate into large solid masses that can travel by oil and gas transporting pipelines, and potentially block or damage the pipelines and/or related equipment. The damage resulting from a blockage can be very costly from an equipment repair standpoint, as well as from the loss of production, and finally the resultant environmental impact.

The industry uses a number of methods to prevent such blockages such as thermodynamic hydrate inhibitors (THI), anti-agglomerants (AA), and kinetic hydrate inhibitors (KHI). The amount of chemical needed to prevent blockages varies widely depending upon the type of inhibitor that is employed. Thermodynamic hydrate inhibitors are substances that can reduce the temperature at which the hydrates form at a given pressure and water content and are typically used at very high concentrations (regularly dosed as high as 50% based on water content—glycol is often used in amounts as high as 100% of the weight of the produced water). Therefore, there is a substantial cost associated with the transportation and storage of large quantities of these solvents.

A more cost-effective alternative is the use of LDHIs, as they generally require less that 2% dose to inhibit the nucleation or growth of gas hydrates. There are two general types of LDHIs, kinetic hydrate inhibitors (KHIs) and anti-agglomerants (AAs), which are both typically used at much lower concentrations (0.3-0.5% active concentration). KHIs work by delaying the growth of gas hydrate crystals and as anti-nucleators. AAs allow the hydrates to form but they prevent them from agglomerating and subsequent accumulation into larger masses capable of causing plugs. An AA enables gas hydrates to form but in the shape of fluid slurry dispersed in the liquid hydrocarbon phase. In general, the water cut should be below 50% otherwise the slurry become too viscous to transport.

There is therefore an ongoing need for new and effective methods of inhibiting the formation of hydrate agglomerates, particularly those that are capable of operating under higher water-cuts.

BRIEF SUMMARY OF THE INVENTION

Accordingly, this invention pertains to anti-agglomerant compositions as well as methods for inhibiting the formation of hydrate agglomerates in an aqueous medium comprising water, gas, and optionally liquid hydrocarbon.

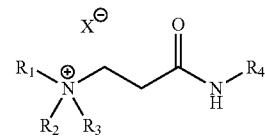

In the above formula, $R_1$, $R_2$, and $R_3$ are each independently $C_nH_{2n+1}$ or benzyl. $R_4$ is $C_4$-$C_{20}$ alkyl or alkenyl. n is an integer from 0 to 10. $X^-$ is a counterion.

In another aspect, the present invention provides for a method of inhibiting the formation of hydrate agglomerates in an aqueous medium comprising water, gas, and optionally liquid hydrocarbon comprising adding to the aqueous medium an effective anti-agglomerating amount of a composition comprising the above formula and optionally salts thereof.

It is an advantage of the invention to provide anti-agglomerant compositions useful for the prevention of hydrate plugs in oil production pipes.

It is another advantage of the invention to provide anti-agglomerant compositions that do not negatively affect the overboard water quality.

It is a further advantage of the invention to provide anti-agglomerant compositions that are capable to be delivered in subsea umbilical lines.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION

The compositions of the invention comprise a generic formula and optionally salts thereof as given below.

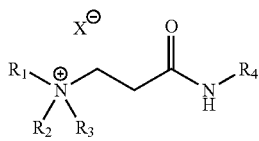

In the above formula, $R_1$, $R_2$, and $R_3$ are each independently $C_nH_{2n+1}$ or benzyl. $R_4$ is $C_4$-$C_{20}$ alkyl or alkenyl. n is an integer from 0 to 10. $X^-$ is a counterion.

"Alkenyl" means a monovalent group derived from a straight, branched, or cyclic hydrocarbon containing at least one carbon-carbon double bond by the removal of a single hydrogen atom from each of two adjacent carbon atoms of an alkyl group. Representative alkenyl groups include, for example, ethenyl, propenyl, butenyl, 1-methyl-2-buten-1-yl, and the like.

"Alkyl" refers to a monovalent group derived by the removal of a single hydrogen atom from a straight or branched chain or cyclic saturated or unsaturated hydrocarbon. Representative alkyl groups include methyl, ethyl, propyl, butyl, pentyl, hexyl, heptyl, octyl, nonyl, and decyl.

"Counterion" refers to a halide selected from fluoride, chloride, bromide, iodide, or carboxylate selected from reaction with mineral acid, acrylic acid, acetic acid, methacrylic acid, glycolic acid, thioglycolic acid, propionic acid, butyric acid, the like, and any combination thereof.

In an embodiment, the composition comprises the following formula and optionally salts thereof. R is at least one or a mixture of saturated or unsaturated $C_8$, $C_{10}$, $C_{12}$, $C_{14}$, $C_{16}$, and $C_{18}$. In embodiments, R is derived from cocoamine.

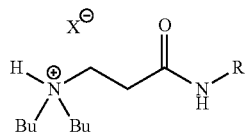

In an embodiment, the composition comprises the following formula and optionally salts thereof. R is at least one or a mixture of saturated or unsaturated $C_8$, $C_{10}$, $C_{12}$, $C_{14}$, $C_{16}$, and $C_{18}$. In embodiments, R is derived from cocoamine ("coco").

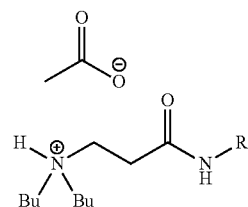

In an embodiment, the composition comprises the following formula and optionally salts thereof.

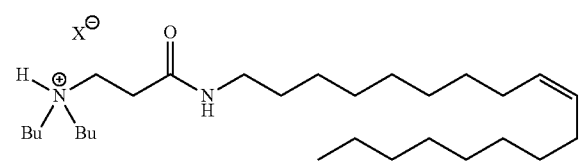

In an embodiment, the composition comprises the following formula and optionally salts thereof.

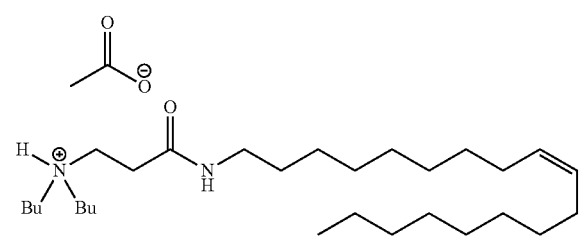

In an embodiment, the composition comprises the following formula and optionally salts thereof.

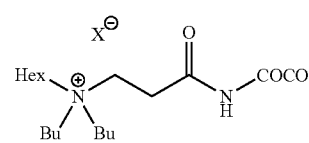

In an embodiment, the composition comprises the following formula and optionally salts thereof.

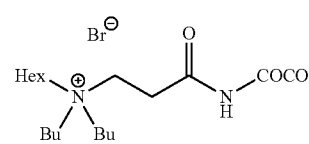

In an embodiment, the composition comprises the following formula and optionally salts thereof.

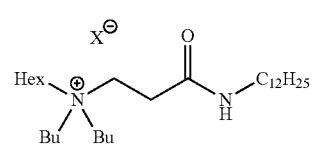

In an embodiment, the composition comprises the following formula and optionally salts thereof.

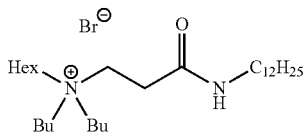

In an embodiment, the composition comprises the following formula and optionally salts thereof.

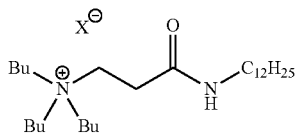

In an embodiment, the composition comprises the following formula and optionally salts thereof.

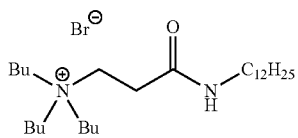

Various synthesis methodologies, which can be appreciated by one of ordinary skill in the art, can be utilized to make the claimed compositions. Detailed representative synthetic schemes are provided in the examples.

The compositions of this invention can contain one or more additional chemistries. Various formulations can be appreciated by one of ordinary skill in the art and can be made without undue experimentation.

In one embodiment, the composition further comprises at least one additional hydrate inhibitor. Exemplary hydrate inhibitors are disclosed in U.S. Pat. No. 8,921,478, "Method of Controlling Gas Hydrates in Fluid Systems," filed Oct. 17, 2008, U.S. Patent Application Publication No. 2010/0099807, "Method of Controlling Gas Hydrates in Fluid Systems," filed Oct. 17, 2008, U.S. Pat. No. 8,334,240, "Compositions and Methods for Inhibiting the Agglomeration of Hydrates in a Process," filed Mar. 9, 2009, and U.S. Pat. No. 8,697,615, "Composition and Method for Reducing Hydrate Agglomeration," filed Dec. 16, 2008, all incorporated herein by reference.

In an embodiment, the invention comprises the following formula and optionally salts thereof (including at least monobutyl amine reactions with 2 equivalents of acrylic acid):

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or nonpolar solvents or a mixture thereof.

In another embodiment, the composition further comprises one or more solvents selected from isopropanol, methanol, ethanol, 2-ethylhexanol, heavy aromatic naphtha, toluene, ethylene glycol, ethylene glycol monobutyl ether (EGMBE), diethylene glycol monoethyl ether, xylene, or a combination thereof.

The composition is introduced into the fluid by any means suitable for ensuring dispersal of the inhibitor through the fluid being treated. Typically the inhibitor is injected using mechanical equipment such as chemical injection pumps, piping tees, injection fittings, and the like. The inhibitor mixture can be injected as prepared or formulated in one or more additional polar or non-polar solvents depending upon the application and requirements.

Representative polar solvents suitable for formulation with the inhibitor composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like.

Representative of non-polar solvents suitable for formulation with the inhibitor composition include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like.

In embodiments of the invention, the disclosed composition is used in a method of inhibiting the formation of hydrate agglomerates in an aqueous medium comprising water, gas, and optionally liquid hydrocarbon. The method comprises adding to the aqueous medium an effective antiagglomerant amount of the disclosed composition.

The composition and method of this invention is effective to control gas hydrate formation and plugging in hydrocarbon production and transportation systems. To ensure effective inhibition of hydrates, the inhibitor composition should be injected prior to substantial formation of hydrates. A preferred injection point for petroleum production operations is downhole near the near the surface controlled sub-sea safety valve. This ensures that during a shut-in, the product is able to disperse throughout the area where hydrates will occur. Treatment can also occur at other areas in the flowline, taking into account the density of the injected fluid. If the injection point is well above the hydrate formation depth, then the hydrate inhibitor should be formulated with a solvent with a density high enough that the inhibitor will sink in the flowline to collect at the water/oil interface. Moreover, the treatment can also be used for pipelines or anywhere in the system where there is a potential for hydrate formation.

In embodiments, the composition is applied to an aqueous medium that contains various levels of salinity. In one embodiment, the fluid has a salinity of 0% to 25%, about 1% to 24%, or about 10% to 25% weight/weight (w/w) total dissolved solids (TDS). The aqueous medium in which the disclosed compositions and/or formulations are applied can be contained in many different types of apparatuses, especially those that transport an aqueous medium from one point to another point.

In embodiments, the aqueous medium is contained in an oil and gas pipeline. In other embodiments, the aqueous medium is contained in refineries, such as separation vessels, dehydration units, gas lines, and pipelines.

In embodiments, the composition is applied to an aqueous medium that contains various levels of water cut. One of ordinary skill in the art would interpret water cut to mean the % of water in a composition containing an oil and water mixture. In one embodiment, the water cut is from 1 to 80% w/w total dissolved solids.

The compositions of the present disclosure and/or formulations thereof can be applied to an aqueous medium in various ways that would be appreciated by of ordinary skill in the art. One of ordinary skill in the art would appreciate these techniques and the various locations to which the compositions or chemistries can be applied.

In one embodiment, the compositions and/or formulations are pumped into the oil/gas pipeline by using an umbilical line. In a further embodiment, capillary string injection systems can be utilized to deliver the compositions and/or formulations of the invention, in this case anti-agglomerants. U.S. Pat. No. 7,311,144 provides a description of an apparatus and methods relating to capillary injection.

Various dosage amounts of a composition and/or formulation can be applied to the aqueous medium to inhibit the formation of hydrate agglomerates. One of ordinary skill in the art would be able to calculate the amount of anti-agglomerant for a given situation without undue experimentation. Factors that would be considered of importance in such calculations include, for example, content of aqueous medium, percentage water cut, API gravity of hydrocarbon, and test gas composition.

In one embodiment, the dose range for the hydrate inhibitor that is applied to an aqueous medium is between about 0.1% volume to about 3% volume based on water cut. In another embodiment, the dose range is from about 0.25% volume to about 1.5% volume based on water cut.

The methodologies described in the present invention may be utilized with other compositions that are commensurate in scope with this disclosure. Other chemistries used for inhibiting the formation of agglomerants in fluids, which are outside the specific generic formula described above, but are commensurate in scope with the claimed compositions generic formula, may be utilized if the system conditions permit the compositions to inhibit the formation of agglomerants (hydrate agglomerates). This protocol can be achieved without undue experimentation, specifically, for example, the rocking test described below can be utilized in determining the effectiveness of a given chemistry.

The foregoing may be better understood by reference to the following examples, which are intended for illustrative purposes and are not intended to limit the scope of the invention.

Example 1

A representative synthetic scheme is given below for the synthesis of N-butyl-N-(3-(cocoamino)-3-oxopropyl)butan-1-aminium acetate.

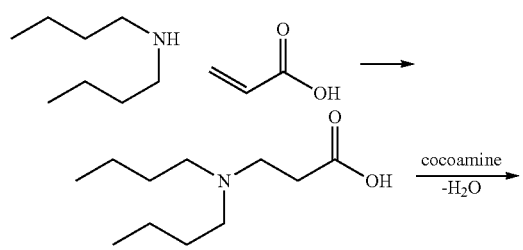

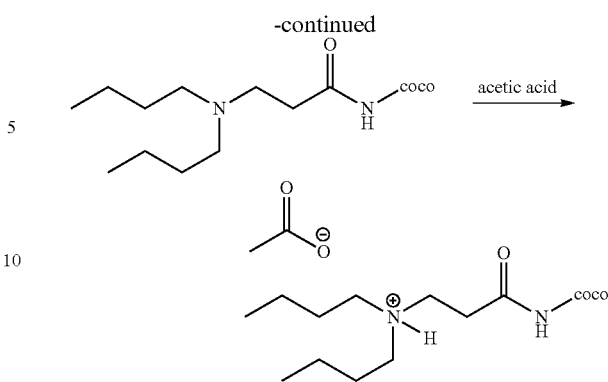

To a 250-mL, 3-neck round bottom flask was added 40.00 g (0.31 mol) dibutylamine and a magnetic stirbar. The flask was fitted with a thermocouple, reflux condenser, and addition funnel containing 22.30 g (0.31 mol) acrylic acid. The acrylate was added to the stirring amine slowly. Once the addition was complete, the addition funnel was replaced with a glass stopper and the reaction mixture was heated at 120° C. for 2 hours. Upon cooling to ambient temperature, an orange solid was formed. Complete conversion was confirmed by the disappearance of the dibutylamine starting material by TLC (1/5 $CHCl_3$/MeOH with 0.5% v/v $NH_4OH$). To the orange solid was added 60.58 g (0.31 mol) cocoamine. An insulated Dean-Stark trap was attached to the apparatus between the flask and reflux condenser for water removal. The reaction mixture was heated at 165° C. for 6 hours at which time TLC analysis (8/1 $CHCl_3$/MeOH with 0.5% v/v $NH_4OH$) confirmed the disappearance of the intermediate carboxylic acid. Upon cooling to ambient temperature a light orange liquid was formed. To the resulting amide at ambient temperature was slowly added 18.59 g (0.31 mmol) acetic acid and the reaction mixture was stirred at ambient temperature for 2 hours.

Example 2

A representative synthetic scheme is given below for the synthesis of N,N-dibutyl-N-(3-(cocoamino)-3-oxopropyl)hexan-1-aminium bromide.

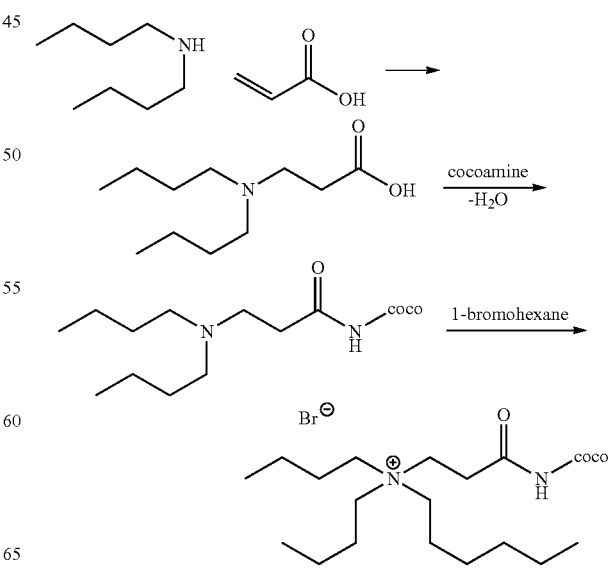

To a 250-mL, 3-neck round bottom flask was added 40.00 g (0.31 mol) dibutylamine and a magnetic stirbar. The flask was fitted with a thermocouple, reflux condenser, and addition funnel containing 22.30 g (0.31 mol) acrylic acid. The acrylate was added to the stirring amine slowly. Once the addition was complete, the addition funnel was replaced with a glass stopper and the reaction mixture was heated at 120° C. for 2 hours. Upon cooling to ambient temperature, an orange solid was formed. Complete conversion was confirmed by the disappearance of the dibutylamine starting material by TLC (1/5 CHCl$_3$/MeOH with 0.5% v/v NH$_4$OH). To the orange solid was added 60.58 g (0.31 mol) cocoamine. An insulated Dean-Stark trap was attached to the apparatus between the flask and reflux condenser for water removal. The reaction mixture was heated at 165° C. for 6 hours at which time TLC analysis (8/1 CHCl$_3$/MeOH with 0.5% v/v NH$_4$OH) confirmed the disappearance of the intermediate carboxylic acid. Upon cooling to ambient temperature a light orange liquid was formed. To the resulting amide at ambient temperature was added 51.09 g (0.31 mol) 1-bromohexane and 42.07 g 2-propanol. The reaction mixture was heated at 97.5° C. for 6 hours.

Example 3

Samples 1 to 4 of Table 1 are the cationic ammonium products of the reaction of acrylic or acetic acid with the adduct formed from the addition of commercially available acrylic acid to dibutylamine followed by amidation with cocoamine. Samples 5 to 10 are the quaternization products of the reaction of 1-chlorobutane, 1-bromobutane, or 1-bromohexane with the adduct formed from the addition of commercially available acrylic acid to dibutylamine followed by amidation with cocoamine. All of the ammonium species are soluble in 2-propanol (IPA), methanol, ethylene glycol (MEG), ethylene glycol monobutyl ether (EGMBE), glycerol, heavy aromatic naphtha (HAN) and combinations thereof. Samples 1 to 10 were dissolved to 40% w/w for the anti-agglomeration test.

TABLE 1

New anti-agglomerant chemistries

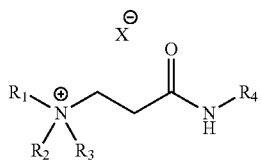

| Sample | R1 | R2 | R3 | R4 | X | Solvent |
|---|---|---|---|---|---|---|
| 1 | C$_4$H$_9$ | C$_4$H$_9$ | H | coco | acrylate | MeOH |
| 2 | C$_4$H$_9$ | C$_4$H$_9$ | H | coco | acetate | MeOH |
| 3 | C$_4$H$_9$ | C$_4$H$_9$ | H | coco | acrylate | IPA |
| 4 | C$_4$H$_9$ | C$_4$H$_9$ | H | coco | acetate | IPA |
| 5 | C$_4$H$_9$ | C$_4$H$_9$ | C$_4$H$_9$ | coco | Cl | IPA/MeOH |
| 6 | C$_4$H$_9$ | C$_4$H$_9$ | C$_4$H$_9$ | coco | Br | IPA/MeOH |
| 7 | C$_4$H$_9$ | C$_4$H$_9$ | C$_6$H$_{13}$ | coco | Br | IPA/MeOH |
| 8 | C$_4$H$_9$ | C$_4$H$_9$ | C$_4$H$_9$ | coco | Cl | IPA/MEG |
| 9 | C$_4$H$_9$ | C$_4$H$_9$ | C$_4$H$_9$ | coco | Br | IPA/MEG |
| 10 | C$_4$H$_9$ | C$_4$H$_9$ | C$_6$H$_{13}$ | coco | Br | IPA/MEG |

The rocking cell test is the primary test for assessing the performance of an anti-agglomerant chemistry. Chemistries are evaluated based on their ability to effectively minimize the size of hydrate agglomerate particles and then disperse those particles into the hydrocarbon phase. Chemical performance is evaluated by determining the maximum treatable water cut (water to oil ratio) and the minimum chemical dosage to register a pass in the rocking cell test.

A rocking cell has two parts, manifold and cell body. The manifold is made of stainless steel fittings weld together. It has three stems. Inlet stem is used to charge gas into the cell. Outlet stem is used to release the gas out of cell. Third steam is connecting to transducer, which measures the pressure inside of the cell. Cell body has three layers. The outer layer is a polycarbonate tube, which thickness is 0.7 cm. The middle layer is made of stainless steel metal, and been connected to the manifold. The inner layer is high-pressure sapphire tube, which outer diameter is 2.8 cm, inner diameter is 1.85 cm, and length is 5 cm. This sapphire tube can handle up 3000 psi. A stainless steel ball of 1.6 cm of diameter is located inside sapphire tube to induce turbulence and mix fluids during the rocking process.

Test fluids usually contain three components. For this anti-agglomerant test, a correct amount of warm Magnolia crude oil is injected into the cell first. Next, a solution of 7% by weight of NaCl and DI water was injected with the accurate amount according to the percent of aqueous phase. Chemical, low dosage hydrate inhibitor, is the final component injected into the cell. The dosage of chemical is based on the volume of aqueous phase. Test was set at 21° C. as initial condition. Each cell is charged by Green Canyon gas and pressurized up to 2,100 psi. All cells rock for at least 1.5 to 2 hours until fluid is saturated and pressure stabilizes. Next, temperature is reduced to the set point of 4° C. Cells rocked for 16 hours, held static for 6 hours, and rocked back for 2 hours. Pressure data is recorded during this time. Observations are taken every two to three hours, before stopped rocking and also immediately after the restart.

TABLE 2

Rocking cell experiment results for new anti-agglomerant chemistries

| Sample | Maximum Water Cut |
|---|---|
| Blank | None |
| Comparative Sample A | 50% |
| Comparative Sample B | 55% |
| 1 | 65% |
| 2 | 65% |
| 3 | 65% |
| 4 | 65% |
| 5 | 55% |
| 6 | 55% |
| 7 | 55% |
| 8 | 55% |
| 9 | 55% |
| 10 | 55% |

The new chemistries provide not only an increase in chemical performance in the rocking cell test, but a significant increase in overboard water quality. Surfactant has a tendency to stabilize emulsion at the oil/water interface. This chemistry has shown in laboratory bottle test experiments to result in enhanced water quality and found to be more reactive with a number of water clarifiers.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A composition comprising the following formula and optionally salts thereof:

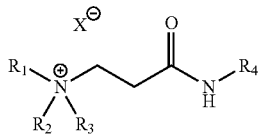

wherein $R_1$ is $C_nH_{2n+1}$ or benzyl;
$R_2$ and $R_3$ are butyl;
wherein R4 is $C_4$-$C_{20}$ alkyl or alkenyl;
n is an integer from 0 to 10; and
$X^-$ is a counterion.

2. The composition of claim 1, wherein each alkyl is independently selected from the group consisting of: a straight chain alkyl, a branched chain alkyl, a cyclic alkyl, a saturated version of the foregoing, an unsaturated version of the foregoing, and combinations thereof.

3. The composition of claim 1, wherein $R_1$ is selected from the group consisting of: methyl; ethyl; propyl; butyl; pentyl; hexyl; heptyl; octyl; nonyl; and decyl.

4. The composition of claim 1, wherein the alkyl for $R_4$ is selected from the group consisting of: butyl; pentyl; hexyl; heptyl; octyl; nonyl; decyl; and combinations thereof.

5. The composition of claim 1, wherein the counterion comprises at least one halide.

6. The composition of claim 1, wherein the counterion is at least one carboxylate.

7. The composition of claim 1, further comprising at least one component selected from: thermodynamic hydrate inhibitors, one or more kinetic hydrate inhibitors, one or more additional anti-agglomerants, and combinations thereof.

8. The composition of claim 1, further comprising at least one component selected from: asphaltene inhibitors, paraffin inhibitors, corrosion inhibitors, scale inhibitors, emulsifiers, water clarifiers, dispersants, emulsion breakers, and combinations thereof.

9. The composition of claim 1, further comprising at least one polar or nonpolar solvent or a mixture thereof.

10. The composition of claim 1, further comprising at least one solvent selected from the group consisting of: isopropanol, methanol, ethanol, 2-ethylhexanol, heavy aromatic naphtha, toluene, ethylene glycol, ethylene glycol monobutyl ether (EGMBE), diethylene glycol monoethyl ether, xylene, and combinations thereof.

11. A method of inhibiting the formation of hydrate agglomerates in a fluid comprising water, gas, and optionally liquid hydrocarbon comprising adding to the fluid an effective anti-agglomerant amount of the composition of claim 1.

12. The method of claim 11, wherein said fluid has a salinity of 0% to 25% w/w percent total dissolved solids (TDS).

13. The method of claim 11, wherein the fluid is contained in an oil or gas pipeline or refinery.

* * * * *